(12) United States Patent
Schibli et al.

(10) Patent No.: US 11,213,254 B2
(45) Date of Patent: Jan. 4, 2022

(54) IMPLANTABLE SENSOR

(71) Applicant: Heraeus Deutschland GmbH & Co. KG, Hanau (DE)

(72) Inventors: Stefan Schibli, Frankfurt am Main (DE); Jens Troetzschel, Ronneburg (DE); Thomas Doerge, Neunkirchen (DE); Murad Abu Asal, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 550 days.

(21) Appl. No.: 15/249,248

(22) Filed: Aug. 26, 2016

(65) Prior Publication Data

US 2017/0055909 A1 Mar. 2, 2017

(30) Foreign Application Priority Data

Aug. 28, 2015 (EP) .................................. 15182859

(51) Int. Cl.
| | |
|---|---|
| *A61B 5/00* | (2006.01) |
| *A61B 5/0215* | (2006.01) |
| *A61B 5/03* | (2006.01) |
| *A61B 5/01* | (2006.01) |
| *A61B 3/16* | (2006.01) |

(Continued)

(52) U.S. Cl.
CPC .............. *A61B 5/6861* (2013.01); *A61B 3/16* (2013.01); *A61B 5/0031* (2013.01); *A61B 5/01* (2013.01); *A61B 5/0215* (2013.01); *A61B 5/036* (2013.01); *A61B 5/076* (2013.01); *A61B 5/1126* (2013.01); *A61B 5/0008* (2013.01); *A61B 5/6882* (2013.01); *A61B 2090/3966* (2016.02); *A61B 2560/0219* (2013.01); *A61B 2562/0223* (2013.01); *A61B 2562/0247* (2013.01); *A61B 2562/0261* (2013.01); *A61B 2562/0285* (2013.01)

(58) Field of Classification Search
CPC ..... A61B 5/6882; A61B 5/6861; A61B 5/036; A61B 5/0215; A61B 5/0031; A61B 2562/0285; A61B 2562/0261; A61B 2562/0247; A61B 2560/0219; A61B 2090/3966
See application file for complete search history.

(56) References Cited

U.S. PATENT DOCUMENTS 6,511,508 B1 * 1/2003 Shahinpoor ............. A61F 2/147
600/37
9,849,289 B2 * 12/2017 Mashiach ............ A61N 1/0526
(Continued)

FOREIGN PATENT DOCUMENTS

| GB | 2464981 | 5/2010 |
|---|---|---|
| WO | 2005027998 | 3/2005 |

(Continued)

*Primary Examiner* — Joanne M Hoffman
*Assistant Examiner* — Milton Truong
(74) *Attorney, Agent, or Firm* — Dicke, Billig & Czaja, PLLC

(57) ABSTRACT

An implantable sensor is proposed including a ring shaped element and a coil. The ring shaped element is made of a silicone and is electrically conductive. The coil may be formed by a wire with a number of windings, wherein at least the free ends of the wire are enclosed by the silicone of the ring shaped element, wherein an electrical resistance of the ring shaped element varies upon a deformation of the ring shaped element.

20 Claims, 2 Drawing Sheets

(51) Int. Cl.
*A61B 5/07* (2006.01)
*A61B 5/11* (2006.01)
*A61B 90/00* (2016.01)

(56) References Cited

U.S. PATENT DOCUMENTS

| | | | |
|---|---|---|---|
| 2006/0173397 A1* | 8/2006 | Tu | A61F 9/00781 604/8 |
| 2007/0270934 A1* | 11/2007 | Stern | A61B 5/0002 623/1.11 |
| 2008/0208065 A1* | 8/2008 | Aebersold | A61B 5/0031 600/488 |
| 2009/0088838 A1* | 4/2009 | Shaolian | A61F 2/2445 623/2.37 |
| 2010/0210939 A1* | 8/2010 | Hartmann | A61B 5/062 600/424 |
| 2010/0249920 A1* | 9/2010 | Bolling | A61B 17/0644 623/2.11 |
| 2010/0324476 A1 | 12/2010 | Boukhny et al. | |
| 2011/0015512 A1* | 1/2011 | Pan | A61B 3/16 600/399 |
| 2011/0288395 A1* | 11/2011 | Elsheikh | A61B 3/16 600/398 |
| 2012/0232478 A1* | 9/2012 | Haslinger | A61M 25/0012 604/103.09 |
| 2013/0213140 A1* | 8/2013 | Eichhorn | G01L 9/0035 73/774 |

FOREIGN PATENT DOCUMENTS

| | | |
|---|---|---|
| WO | 2009111726 | 9/2009 |
| WO | 2012137067 | 10/2012 |

* cited by examiner

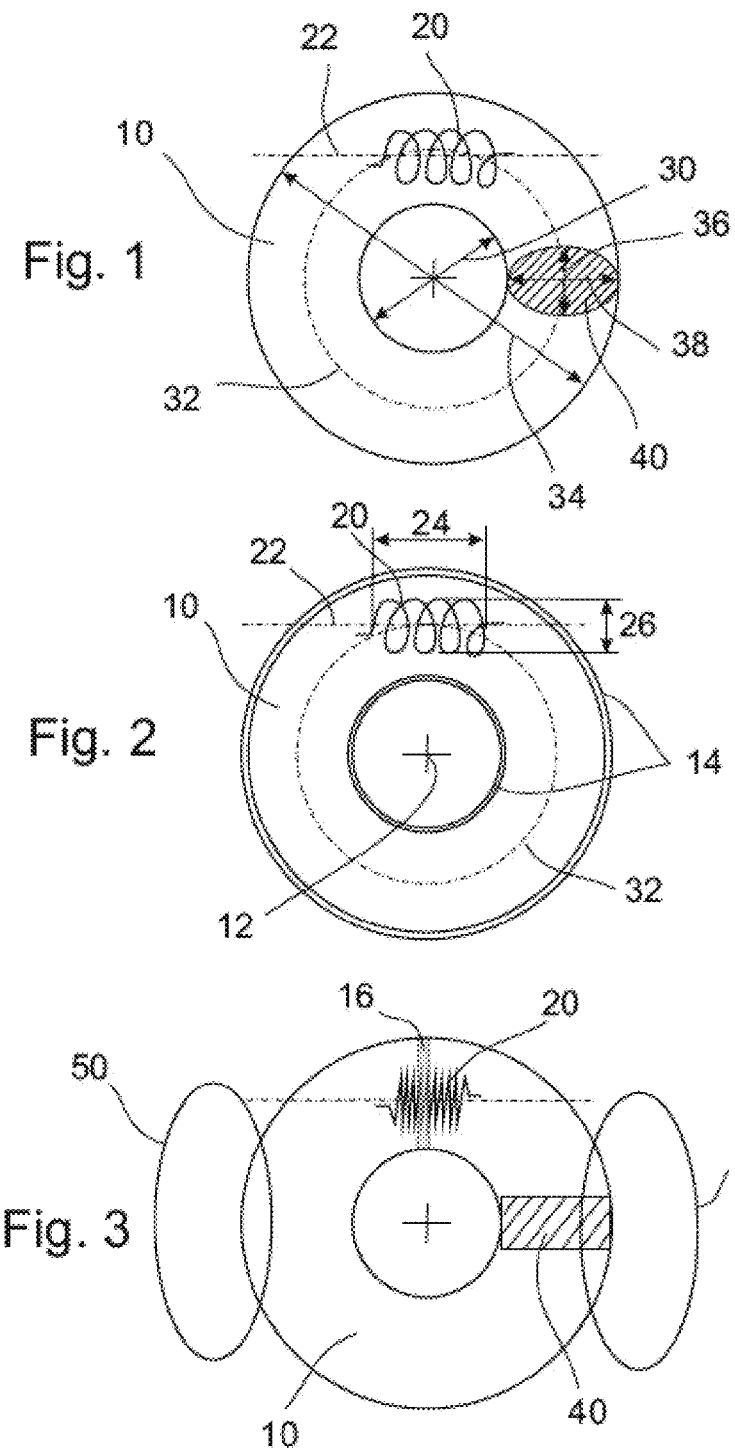

IMPLANTABLE SENSOR

CROSS-REFERENCE TO RELATED APPLICATIONS

This Utility Patent Application claims priority to European Patent Application No. EP 15182859.7, filed on Aug. 28, 2015, which is incorporated herein by reference.

BACKGROUND

One aspect relates to a sensor. One aspect relates to an implantable sensor. In a human body, several situations may exist in which it is of interest to measure a pressure or a temperature for diagnostic purposes. One possibility suggested in the art is to provide a wireless sensor which is configured to be implanted. By way of such wireless sensors, for example a pressure within the brain, an eye or lungs can be measured.

EP 1 677 852 describes a method of monitoring the pressure within an aneurysm sac that has undergone repair by implantation of an endograft to be able to identify the potential presence of endoleaks, by placing a device capable of measuring pressure within the aneurysm sac at the time of endograft insertion. By utilizing an external device to display the pressure being measured by the sensor, the physician will obtain an immediate assessment of the success of the endograft at the time of the procedure, and patient follow-up visits will allow simple monitoring of the success of the endograft implantation. The implantable device utilizes coil-capacitor-circuit and changes in the resonance frequency of the same to measure a corporeal parameter such as pressure, temperature, or both. Specific target locations could include the interior of an abdominal aneurysm or a chamber of the heart.

That device is of relatively large size due to the high number of components including ceramic components, which in turn results in a complex and expensive manufacturing process. Further, a specific catheter is needed to implant the sensor.

Another device is available for measuring the pressure in an eye, which device includes a completely encapsulated micro-electronic chip and a coil by means of which electrical current can be induced into the chip and the chip can be read out.

However, such a micro-electronic chip is complex and expensive, and needs a substantial amount of current so that the coil must be large. A sensor with such a chip is not flexible and must be implanted together with an artificial eye lense.

Known sensors for measuring a pressure in a brain suffer from comparable problems.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The embodiments will now be detailed by way of exemplary embodiments with reference to the attached drawings.

FIG. 1 is an illustration of a sensor according to a first embodiment.

FIG. 2 is an illustration of a sensor according to a second embodiment.

FIG. 3 is an illustration of a sensor according to a third embodiment.

Figure 4:
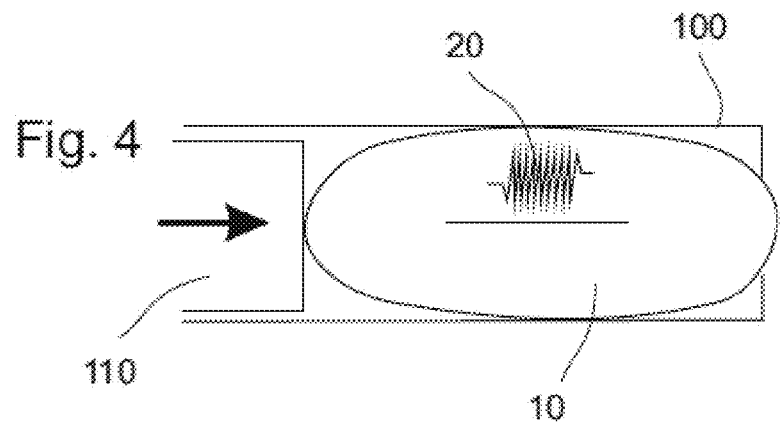
FIG. 4 schematically illustrates a sensor accommodated in a catheter.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present embodiments will now be described in detail with reference to the figures, it is done so in connection with the illustrative embodiments and is not limited by the particular embodiments illustrated in the figures, as defined by the appended claims.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the invention. The following detailed description, therefore, is not to be taken in a limiting sense, and the scope of the invention is defined by the appended claims.

It is to be understood that the features of the various exemplary embodiments described herein may be combined with each other, unless specifically noted otherwise.

Embodiments of implantable sensors are shown in the figures and described in the following.

One aspect of the embodiments may be to provide an implantable wireless sensor which overcomes or at least mitigates the above mentioned problems.

This is achieved by the subject-matter of the independent claim. Further embodiments are described in the dependent claims.

In general, an implantable sensor includes a ring shaped element and a coil. The ring shaped element is made of a silicone and is electrically conductive. The coil may be formed by a wire with a number of windings, wherein at least the free ends of the wire, that is, of the coil are enclosed by the silicone of the ring shaped element.

An external magnetic field induces an electrical current in the coil of the sensor, which current may then flow through the electrically conductive ring. As the electrical resistance of the electrically conductive ring varies upon any kind of deformation of the elastically deformable ring shaped element, the amount of electrical current flowing through the same will be influenced. As a result, a magnetic field generated in the coil by the current flowing through the coil will also be influenced. Measuring the magnetic field and changes in the magnetic field generated by the coil of the sensor allows for a determination of a pressure or a temperature or a tissue movement at the location of the implanted sensor.

The following geometrical definitions will be used throughout the following disclosure. The ring shaped element has an inner diameter, an outer diameter and a thickness. The ring shaped element may also be defined as extending along a ring line and having a cross section. The ring line may, for example, have a diameter being a mean diameter between the inner and outer diameter. A ring plane may be defined as including the ring line. The diameters may be measured within that plane and through a center point of the ring.

The thickness of the ring shaped element may be measured perpendicular to the ring plane. It is noted that the ring shaped element must not be circular but may also have any other shape like rectangular or elliptical. A width of the ring may be calculated as half of the outer diameter minus half of the inner diameter. Preferably, the ring shaped element may have a constant width.

Furthermore, the cross sectional surface of the ring shaped element may be defined by the thickness and the width. The two-dimensional cross sectional surface may thus be measured in a section plane, the section plane including the centre point of the ring and being perpendicular to the ring plane. The cross section of the ring shaped element may have any shape out of the group consisting of square, rectangular, rounded, oval and circular. The sensor may have a smooth contour.

It will be understood that "smooth" refers to a shape without any edges. That is, the outer surface of the sensor may be formed without any discontinuities. Any edges may be provided at least with a chamfer or may be rounded so as to be smooth, i.e. that is, so as to not form any edge at which irritations of soft tissue may occur when the tissue is in contact with the sensor.

The coil has a length and a diameter. The length of the coil may be measured along a main axis of the coil or along the ring line, whereas the diameter of the coil may be measured in the section plane. Consequently, a center axis or main axis of the coil may extend tangentially to or substantially parallel to the ring line.

According to an embodiment is the electrically conductive ring shaped element made of a charged silicone, for example, a silicone charged with particles or nano tubes providing electrically conductivity. The electrically conductivity of such a material can be adjusted by the amount of nano tubes or particles per volume unit, as well as by the distribution of the tubes or particles in the ring shaped element, which distribution may also be inhomogeneous. The silicone may thus have a predetermined, specific resistance comparable to a semiconductor. The resistance may be between 1 kOhm and 2 kOhm, for example, approximately 1.5 kOhm at atmospheric pressure. The resistance will decrease with increasing pressure.

According to an embodiment is the coil of the sensor formed by a wire having a diameter of less than 1 mm, preferably less than 0.5 mm. For example, a wire with a diameter of 0.02 mm allows providing a coil with up to 100 windings at a length of 2 mm. The diameter of the coil may be smaller than the thickness of the ring shaped element so that the complete coils may be arranged within the ring shaped element, that is, the coil may be completely enclosed by the silicone of the ring shaped element.

According to an embodiment is the thickness of the ring shaped element smaller than the inner diameter of the ring shaped element.

According to an embodiment is the length of the coil smaller than half of the outer diameter of the ring shaped element. A sensor having such a relation may be compressed so as to fit into a catheter having a smaller diameter than the outer diameter of the ring shaped element.

According to a further embodiment, the sensor may further include an electrically isolating layer on an outer surface of the ring shaped element. The layer may be made from any suitable isolating material, for example from an electrically isolating silicone. Furthermore, the coil may be electrically isolated. The coil may for example be made of an isolated wire or may otherwise be enclosed by an isolating material, for example by molding. An electrically isolated coil may be suitable in a case in which the coil is not completely enclosed by the material of the ring shaped element.

For improving a visibility in an X-ray image, the coil may be made of a radiopaque material. Thus, the coil may serve as a marker allowing a controlled and precise placement of the sensor within a body.

In accordance with another embodiment, the sensor may further include a fixation element for anchoring the sensor in a tissue. This may, for example, be of interest in a situation in which the sensor is intended to be placed at a location of moving structures in a body, for example, in or in the vicinity of a heart. In an exemplary embodiment, the fixation element may be a wire loop or hook extending from the ring shaped element.

According to a further embodiment, the sensor as described above may be a part of a system further including a read out unit for reading out a signal from the sensor. The read out or detecting unit may include at least a coil adapted to generate a magnetic field for contactless inducing an electrical current in the coil of the sensor, and adapted to receive a magnetic field generated by the coil of the sensor. It will be appreciated by a skilled person that the detecting unit may also include a processing unit adapted to interpret values or data related to the magnetic field received from the sensor, and an output or display means for indicating the result of such an interpretation.

It has to be noted that a person skilled in the art will gather from the above and the following description that, unless otherwise notified, in addition to any combination of features belonging to one embodiment, also any combination of features relating to another embodiment is considered to be disclosed with this application.

These and other objects, features and advantages of the exemplary embodiments of the invention will become apparent upon reading the following detailed description of exemplary embodiments, when taken in conjunction with the appended claims.

FIG. 1 is a top view of a first embodiment of a sensor with a ring shaped element 10 and a coil 20.

The ring shaped element 10 extends substantially in the plane of the figure and defines a central axis 12 which extends perpendicular into the figure and through a center of the ring shaped element. The ring shaped element can be described by an inner diameter 30, an outer diameter 34, and a cross section 40. Alternatively, the ring shaped element 10 can be described by a ring line 32 which extends, for example, in the middle of the cross section 40. According to this embodiment, the ring line 32 may have a diameter being a mean diameter between the inner diameter 30 and the outer diameter 34. The cross section 40 of the ring shaped element 10 may be defined by a width 38 and a thickness 36 as well as by an indication of the shape of the contour.

In this first embodiment, the shape of the cross section may be described as being oval. It is noted that the dimensions of the cross section 40 may be large enough so as to completely encompass the coil 20.

FIG. 2 shows a second embodiment of a sensor with a ring shaped element 10 and a coil 20. The second embodiment differs from the first embodiment in that the ring shaped element has a layer 14 made of a non-conductive material, that is, an electrically isolating layer 14. The layer may be provided on the complete outer surface of the ring shaped element 10.

As in the first embodiment, the coil 20 has a diameter 26 and a length 24 and includes a main axis 22 which extends centrally through the winding of the coil. The main axis 22 of the coil 20 extends substantially perpendicular to the central axis 12 of the ring shaped element 10, with a lateral distance between these two axes which distance is approximately half the diameter of the ring line 32. That is, the main axis 22 of the coil 20 may extend tangentially to the ring line, at least at one point through the center of the cross section 40 of the ring shaped element. It is noted that the coil may also be curved so as to have a curved main axis which may more or less follow the ring line 32 defining the ring shaped element.

FIG. 3 shows a third embodiment of a sensor with a ring shaped element 10, a coil 20 and fixation elements 50. For example, the coil 20 as well as the cross section 40 are shown with other shapes as in the previous embodiments. It will be understood that these elements may have further shapes which provide the same intended functionality. The coil 20 may have more or less windings and may have larger or smaller diameter and length, respectively, and will furthermore be capable to induce an electrical current in response to a magnetic field, and vice versa. The cross section 40 which is rectangular in FIG. 3, may also be a combination of a rounded shape as in FIG. 1 and a square or rectangular shape as in FIG. 3.

Further shown in FIG. 3 is a line 16 which line shall indicate that the conductivity of the ring shaped element may be interrupted or at least reduced or restricted in the region of the coil. That is, there may be a cap in the ring shaped element without any material, or there may be an isolating slice, or there may be a region in the ring shaped element having less or no electrically conductive nano tubes or particle.

Each of the two fixation elements 50 of the third embodiment may be formed by an elastic wire, wherein the wire may be made from a material which is not conductive. It is noted that the sensor may have only one fixation element but also a plurality of fixation elements, for example, more than two. Furthermore, the fixation element 50 must not be a closed loop but may also be a hook or just an elongated pin extending from the ring shaped element 10 so as to provide the functionality of anchoring the sensor at a location in a body.

It is noted that the embodiments of FIGS. 1 to 3 are shown with the ring shaped element in a relaxed condition, that is, without any pressure or force applied to the ring shaped element.

As can be seen in FIG. 4, the sensor, that is, the ring shaped element may be elastically deformed so as to be accommodated in a catheter 100 having a smaller outer diameter than the outer diameter of the sensor. The ring shaped element 10 may thus be compressed to an elongated condition in which the ring shaped element has a first dimension being larger than the outer diameter in a relaxed condition, and has a second dimension being smaller than the outer diameter in the relaxed condition. In one embodiment, the coil 20 is arranged so that the main axis of the coil extends parallel to the larger dimension.

In the example shown in FIG. 4, the catheter 100 may have a pusher 110 by means of which the sensor may be pressed or pushed out of, for example, the distal end of the catheter at an intended implantation site. The elastic ring shaped element 10 will take its relaxed condition after being released from the catheter and will thus allow measurements at the implantation site.

Figure 5:
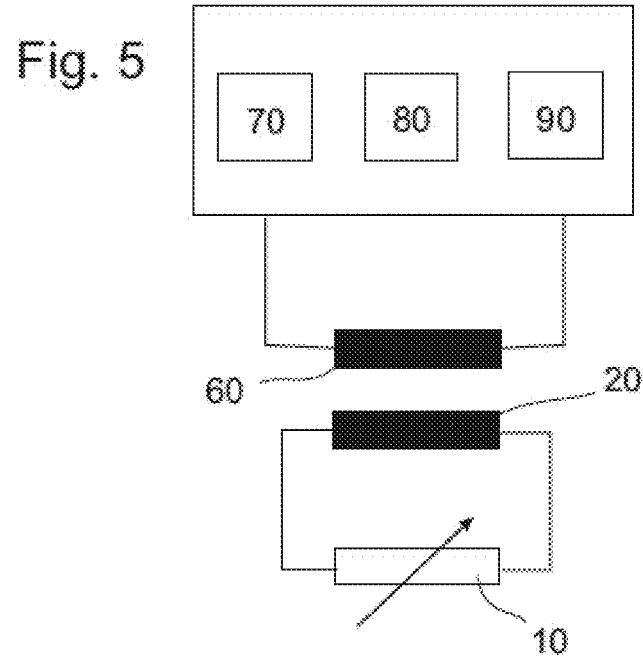
FIG. 5 schematically illustrates a system including a sensor.

FIG. 5 illustrates a system with a sensor and a read out unit. The sensor, which sensor is schematically illustrated in FIG. 5, includes a ring shaped element 10, being shown as a variable resistor, and a coil 20. The read out unit includes a coil 60, an energy source 70 for inducing a magnetic field in the coil 60, a processing unit 80 for processing signals related to values and/or a variation of the magnetic field of the coil 20 as detected by the coil 60, and a display 90 for displaying results.

Practically, the sensor may be implanted into a body by means of a small catheter and immediately after the implantation a first measurement may be performed so as to have a first value. In future measurements, the values may be compared with the first value and based on such a comparison an assessment of physiological conditions may be done.

While embodiments have been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practising the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

Although specific embodiments have been illustrated and described herein, it will be appreciated by those of ordinary skill in the art that a variety of alternate and/or equivalent implementations may be substituted for the specific embodiments shown and described without departing from the scope of the invention. This application is intended to cover any adaptations or variations of the specific embodiments discussed herein. Therefore, it is intended that this invention be limited only by the claims and the equivalents thereof.

What is claimed is:

1. A sensor configured for implantation into a human body comprising:
   a ring shaped element having an inner diameter, an outer diameter and a thickness, the ring shaped element being made of electrically conductive silicone material; and
   a coil having a length, a diameter and first and second open ends on opposite sides of the coil, wherein the coil generates an electrical signal by electromagnetic induction,
   wherein at least the first and second open ends of the coil are enclosed by the silicone of the ring shaped element such that the coil and ring shaped element are coupled in series so that the generated electrical signal flows from the first open end of the coil through the ring shaped element and then to the second open end of the coil, wherein an electrical resistance of the electrically conductive silicone material varies upon a deformation of the electrically conductive silicone material.

2. The sensor of claim 1, wherein the ring shaped element comprises a nano tube charged silicone.

3. The sensor of claim 1, wherein the coil comprises a wire having a diameter of less than 1 mm.

4. The sensor of claim 1, wherein the coil comprises a wire having a diameter of less than 0.5 mm.

5. The sensor of claim 1, wherein the thickness of the ring shaped element is smaller than the inner diameter of the ring shaped element.

6. The sensor of claim 1, wherein the diameter of the coil is smaller than the thickness of the ring shaped element.

7. The sensor of claim 1, wherein the length of the coil is smaller than half of the outer diameter of the ring shaped element.

8. The sensor of claim 1, further comprising a layer on an outer surface of the ring shaped element, wherein the layer is made of an isolating material.

9. The sensor of claim 8, wherein the isolating material of the layer comprises a silicone being electrically isolating.

10. The sensor of claim 1, wherein the sensor is elastically deformable so that the sensor can be accommodated in a catheter with a diameter being smaller than the outer diameter of the ring shaped element.

11. The sensor of claim 1, further comprising an electrically isolating material covering the coil.

12. The sensor of claim 1, wherein the coil comprises a radiopaque material.

13. The sensor of claim 1, further comprising a fixation element for anchoring the sensor in a tissue.

14. A system comprising:
a sensor comprising a ring shaped element and a sensor coil;
wherein the ring shaped element has an inner diameter, an outer diameter and a thickness, the ring shaped element being made of electrically conductive silicone material;
wherein the sensor coil has a length, a diameter and first and second open ends on opposite sides of the sensor coil, wherein at least the first and second open ends of the sensor coil are enclosed by the silicone of the ring shaped element such that the coil and ring shaped element are coupled in series so that current from the first open end of the coil flows through the ring shaped element and then to the second open end of the coil, and wherein an electrical resistance of the ring shaped element varies upon a deformation of the electrically conductive silicone material;
a read out unit for reading out a signal from the sensor, the read out unit comprising a read out coil adapted to generate a magnetic field for contactless inducing an electrical current in the sensor coil, and adapted to receive a magnetic field generated by the sensor coil.

15. The system of claim 14, wherein the ring shaped element comprises a nano tube charged silicone.

16. The system of claim 14, wherein the sensor coil comprises a wire having a diameter of less than 0.5 mm.

17. The system of claim 14, wherein the thickness of the ring shaped element is smaller than the inner diameter of the ring shaped element.

18. The system of claim 14, wherein the diameter of the sensor coil is smaller than the thickness of the ring shaped element.

19. The system of claim 14, further comprising a layer on an outer surface of the ring shaped element, wherein the layer is made of an isolating material.

20. The system of claim 14, further comprising an electrically isolating material covering the sensor coil.

* * * * *